(12) United States Patent
Pavlik

(10) Patent No.: US 11,834,646 B2
(45) Date of Patent: Dec. 5, 2023

(54) METHOD OF ACTUATION OF AN ALTERNATING TANGENTIAL FLOW DIAPHRAGM PUMP

(71) Applicant: Repligen Corporation, Waltham, MA (US)

(72) Inventor: Rudolf Pavlik, Waltham, MA (US)

(73) Assignee: Repligen Corporation, Waltham, MA (US)

( * ) Notice: Subject to any disclaimer, the term of this patent is extended or adjusted under 35 U.S.C. 154(b) by 0 days.

(21) Appl. No.: 17/752,345

(22) Filed: May 24, 2022

(65) Prior Publication Data
US 2022/0282204 A1 Sep. 8, 2022

Related U.S. Application Data

(63) Continuation of application No. 16/908,225, filed on Jun. 22, 2020, now Pat. No. 11,578,301, which is a (Continued)

(51) Int. Cl.
*F04B 49/20* (2006.01)
*F04B 23/04* (2006.01)
(Continued)

(52) U.S. Cl.
CPC .............. *C12M 41/48* (2013.01); *B01D 61/20* (2013.01); *B01D 61/22* (2013.01); *B01D 61/58* (2013.01);
(Continued)

(58) Field of Classification Search
CPC ...... C12M 41/48; C12M 29/00; C12M 29/04; C12M 29/18; C12M 41/00; C12M 41/44;
(Continued)

(56) References Cited

U.S. PATENT DOCUMENTS 4,319,897 A 3/1982 Labadie
4,468,222 A 8/1984 Lundquist
(Continued)

FOREIGN PATENT DOCUMENTS

CN 104863843 A 8/2015
CN 106881058 A 6/2017
(Continued)

OTHER PUBLICATIONS

English Translation of Patent Publication CZ20033483A3, Brock, published May 2004 (Year: 2004).*
(Continued)

*Primary Examiner* — Joseph W Drodge
(74) *Attorney, Agent, or Firm* — KDW Firm PLLC

(57) ABSTRACT

A control unit includes a first connector configured to connect a proportional pressure regulator to a positive pressure supply and a second connector configured to connect the proportional pressure regulator to a negative pressure supply. The control unit further includes at least one sensor configured to detect an amount of air flow (volume per unit of time), positive or negative, within an air flow line connected to an output of the proportional pressure regulator, and a third connector configured to connect the air flow line to an air side of a diaphragm. Additionally, the control unit includes a controller programmed to control at least an opening and closing function of the proportional pressure regulator to attain a desired amount of air flow (volume per unit of time), positive or negative, within the air flow line.

18 Claims, 4 Drawing Sheets

Related U.S. Application Data continuation of application No. 15/892,214, filed on Feb. 8, 2018, now Pat. No. 10,774,297.

(60) Provisional application No. 62/541,023, filed on Aug. 3, 2017.

(51) Int. Cl.

| | | |
|---|---|---|
| *F04B 43/00* | (2006.01) | |
| *F04B 49/06* | (2006.01) | |
| *B01D 61/22* | (2006.01) | |
| *B01D 61/58* | (2006.01) | |
| *B01D 63/02* | (2006.01) | |
| *B01D 61/20* | (2006.01) | |
| *F04B 23/02* | (2006.01) | |
| *C12M 1/36* | (2006.01) | |
| *C12M 1/34* | (2006.01) | |
| *C12M 1/00* | (2006.01) | |
| *F04B 43/073* | (2006.01) | |

(52) U.S. Cl.
CPC ............. *B01D 63/02* (2013.01); *C12M 29/00* (2013.01); *C12M 29/04* (2013.01); *C12M 29/18* (2013.01); *C12M 41/00* (2013.01); *C12M 41/44* (2013.01); *C12M 47/02* (2013.01); *C12M 47/10* (2013.01); *F04B 23/04* (2013.01); *F04B 43/0081* (2013.01); *F04B 43/073* (2013.01); *F04B 49/065* (2013.01); *F04B 49/20* (2013.01); *B01D 2311/2688* (2013.01); *F04B 23/02* (2013.01); *F04B 2205/09* (2013.01)

(58) Field of Classification Search
CPC ...... C12M 47/02; C12M 47/10; C12M 41/36; C12M 29/10; C12M 29/14; C12M 41/30; B01D 61/20; B01D 61/22; B01D 61/58; B01D 63/02; B01D 2311/2688; B01D 29/11; B01D 29/50; B01D 29/52; B01D 29/60; B01D 29/608; B01D 29/88; B01D 29/90; B01D 29/92; B01D 35/26; B01D 35/30; B01D 35/301; B01D 61/18; B01D 63/06; B01D 69/08; B01D 2201/202; B01D 2201/20; B01D 2201/204; B01D 2201/54; B01D 2221/10; B01D 2311/06; B01D 2311/14; B01D 2311/16; B01D 2311/165; B01D 2313/243; B01D 2317/04; B01D 2319/04; F04B 23/04; F04B 43/0081; F04B 43/073; F04B 49/065; F04B 49/20; F04B 23/02; F04B 2205/09; F04B 53/20; F04B 43/023; F04B 43/06; F04B 9/00; F04B 9/02; F04B 9/08; F04B 9/10; F04B 9/103; F04B 9/109; F04B 9/12; F04B 9/125; F04B 19/02; F04B 19/022; F04B 23/00; F04B 23/06; F04B 23/08; F04B 23/103; F04B 23/106; F04B 23/1214; F04B 43/02; F04B 43/04; F04B 43/0054; F04B 43/0063; F04B 43/0072; F04B 43/009; F04B 43/09; F04B 43/086; F04B 45/04; F04B 45/047; F04B 45/053; F04B 45/065; F04B 45/067; F04B 45/073; F04B 49/00; F04B 49/007; F04B 49/02; F04B 49/10; F04B 2201/0201; F04B 2205/00; F04B 2205/01; F04B 2205/03; F04B 2205/14; A61M 1/3403; A61M 1/341; A61M 1/3489; A61M 1/3607; A61M 2205/33; A61M 2205/3327
See application file for complete search history.

(56) References Cited

U.S. PATENT DOCUMENTS

| | | | |
|---|---|---|---|
| 5,257,914 A | 11/1993 | Reynolds | |
| 5,334,497 A | 8/1994 | Inaba | |
| 5,423,738 A | 6/1995 | Robinson | |
| 5,947,689 A | 9/1999 | Schick | |
| 6,085,940 A | 7/2000 | Ferri, Jr. | |
| 6,544,424 B1 | 4/2003 | Shevitz | |
| 8,292,594 B2 | 10/2012 | Tracey | |
| 8,845,902 B2 | 9/2014 | Pralong | |
| 9,550,969 B2 | 1/2017 | Chotteau | |
| 9,663,753 B2 | 5/2017 | Gebauer | |
| 10,166,497 B1 | 1/2019 | Pavlik | |
| 10,774,297 B2 | 9/2020 | Pavlik | |
| 10,792,594 B2 | 10/2020 | Pavlik | |
| 10,799,816 B2 | 10/2020 | Pavlik | |
| 11,578,301 B2 * | 2/2023 | Pavlik | ...................... F04B 53/20 |
| 11,578,302 B2 * | 2/2023 | Pavlik | ...................... F04B 23/04 |
| 2003/0036192 A1 | 2/2003 | Singh | |
| 2004/0159616 A1 | 8/2004 | Cohee | |
| 2004/0259240 A1 | 12/2004 | Fadden | |
| 2006/0019385 A1 | 1/2006 | Smith | |
| 2006/0027500 A1 | 2/2006 | Schick | |
| 2006/0163125 A1 | 7/2006 | Olivier | |
| 2007/0177985 A1 * | 8/2007 | Walls | ...................... F04B 49/10 |
| | | | 417/44.2 |
| 2008/0175719 A1 | 7/2008 | Tracey | |
| 2009/0042253 A1 | 2/2009 | Hiller | |
| 2009/0132094 A1 * | 5/2009 | Laverdiere | ............... F04B 43/02 |
| | | | 222/336 |
| 2009/0173676 A1 * | 7/2009 | Wolbers | ................ F04B 43/073 |
| | | | 210/321.72 |
| 2011/0189029 A1 | 8/2011 | Van De Velde | |
| 2012/0051945 A1 * | 3/2012 | Orndorff | ............... F04B 49/065 |
| | | | 417/279 |
| 2013/0059371 A1 | 3/2013 | Shevitz | |
| 2013/0270165 A1 | 10/2013 | Shevitz | |
| 2013/0319944 A1 * | 12/2013 | Pralong | ................... B01D 61/20 |
| | | | 210/257.2 |
| 2015/0164690 A1 | 6/2015 | Peterson | |
| 2015/0166957 A1 | 6/2015 | Kusters | |
| 2015/0247114 A1 | 9/2015 | Gebauer | |
| 2015/0298035 A1 | 10/2015 | Jay | |
| 2015/0299630 A1 | 10/2015 | Roulston | |
| 2016/0108350 A1 | 4/2016 | Kiyama | |
| 2016/0222337 A1 | 8/2016 | Serway | |
| 2016/0319234 A1 | 11/2016 | Song | |
| 2016/0363118 A1 | 12/2016 | Sakai | |
| 2017/0037421 A1 | 2/2017 | Blessing | |

FOREIGN PATENT DOCUMENTS

| | | | | |
|---|---|---|---|---|
| CZ | 20033483 A3 * | 5/2004 | ............. | F04B 43/06 |
| EP | 1131559 B1 | 7/2005 | | |

OTHER PUBLICATIONS

European Search Report and Written Oppinion for Application No. EP22185523, dated Oct. 27, 2022, 17 pages.
International Preliminary Report on Patentability for PCT/US2018/045033, dated Feb. 13, 2020, 8 pages.
International Search Report and Written Opinion for PCT/US2018/045033, dated Dec. 6, 2018, 11 pages.
European Search Report and Written Opinion for the Application dated Nov. 17, 2020, 18840993.2, 12 pages.
European Search Report and Written Opinion for Application No. EP22185529, dated Oct. 17, 2022, 14 pages.

(56) References Cited

OTHER PUBLICATIONS

European Search Report and Written Opinion for Application No. EP22185532, dated Oct. 18, 2022, 12 pages.

* cited by examiner

METHOD OF ACTUATION OF AN ALTERNATING TANGENTIAL FLOW DIAPHRAGM PUMP

CROSS-REFERENCE TO RELATED APPLICATION

This application is a continuation of U.S. nonprovisional patent application Ser. No. 16/908,225, filed Jun. 22, 2020, which is a continuation of U.S. nonprovisional patent application Ser. No. 15/892,214, filed Feb. 8, 2018, now granted as U.S. Pat. No. 10,774,297, which claims the benefit of and priority under 35 U.S.C. § 119 to U.S. provisional patent application Ser. No. 62/541,023, filed Aug. 3, 2017, the entirety of which applications are incorporated by reference herein for all purposes.

FIELD

The present application relates generally to actuation of diaphragm pumps, and more particularly, to methods, apparatuses and systems for the same.

BACKGROUND

Diaphragm-operated pumps use positive and negative air flow to provide liquid transfer. However, conventional systems do not precisely control the change between positive and negative air flow or the amount of positive and negative air flow. Moreover, such systems often have complicated structures that are difficult to manufacture and maintain, and include air flow restrictions.

SUMMARY

The present application discloses a control unit comprising a first connector configured to connect a proportional pressure regulator to a positive pressure supply; a second connector configured to connect the proportional pressure regulator to a negative pressure supply; at least one sensor configured to detect an amount of air flow (volume per unit of time), positive or negative, within an air flow line connected to an output of the proportional pressure regulator; a third connector configured to connect the air flow line to an air side of a diaphragm; and a controller programmed to control at least an opening and closing function of the proportional pressure regulator to attain a desired amount of air flow (volume per unit of time), positive or negative, within the air flow line.

The present application further discloses a method of actuating a diaphragm pump comprising selecting a volume or size of a diaphragm pump; selecting a volume of a fluid to be displaced by the diaphragm pump over a given period of time; selecting a duration of a pumping operation, which together with the desired volume of fluid to be displaced over said duration, generates a performance profile appropriate for a specific application; actuating the pumping operation by alternating a supply of positive and negative air flow in an air flow line connected at one end to an air side of the diaphragm pump and connected at an opposite end to an output of an air flow regulator; monitoring an amount of air flow within the air flow line to maintain or alter a volume of air flowing per unit of time within the air flow line; optionally, monitoring a position of a diaphragm of the diaphragm pump at one or both ends of its displacement; and optionally, altering the volume of air flowing per unit of time within the air flow line to influence either the position of the diaphragm at one or both ends of its displacement or a duration of a partial or full cycle of displacement or both.

The present application still further discloses a method of controlling a diaphragm pump, comprising actuating a pumping operation of fluid from a first container by alternating a supply of positive and negative air flow to an air side of a diaphragm pump through an air flow line connected to an output of an air flow regulator; suctioning fluid from the first container by applying a supply of negative air flow to the air side of the diaphragm pump; regulating a duration of a partial or full cycle of displacement of the diaphragm pump; filtering the fluid suctioned from the first container; and extracting the filtered fluid so as to direct part of the filtered fluid back to the first container and to direct part of the filtered fluid to a second container.

The present application additionally discloses a method of controlling a diaphragm pump with a controller, comprising alternating between supplying a positive and negative air flow to an air side of a diaphragm pump to actuate pumping of a fluid associated with a bioreactor; suctioning fluid from the bioreactor by supplying a negative air flow to the air side of the diaphragm pump; filtering the fluid suctioned from the bioreactor; extracting the filtered fluid to direct same to a container; and regulating a duration of a partial or full cycle of displacement of the diaphragm pump, wherein the controller controls delivery of filtered fluid to the container in accordance with a process requirement.

The disclosed embodiments may be modified and employed in various ways. For example, various configurations are readily apparent, including a multiplexed pumping system in which a plurality of pumps may be controlled in a networked environment. Alternative exemplary embodiments relate to other features and combinations of features as may be recited in the claims.

BRIEF DESCRIPTION OF THE DRAWINGS

The disclosure will become more fully understood from the following detailed description, taken in conjunction with the accompanying figures, wherein like reference numerals, symbols or terms generally identify similar components, unless context dictates otherwise, and in which.

PREFERRED EMBODIMENTS

Figure 1:
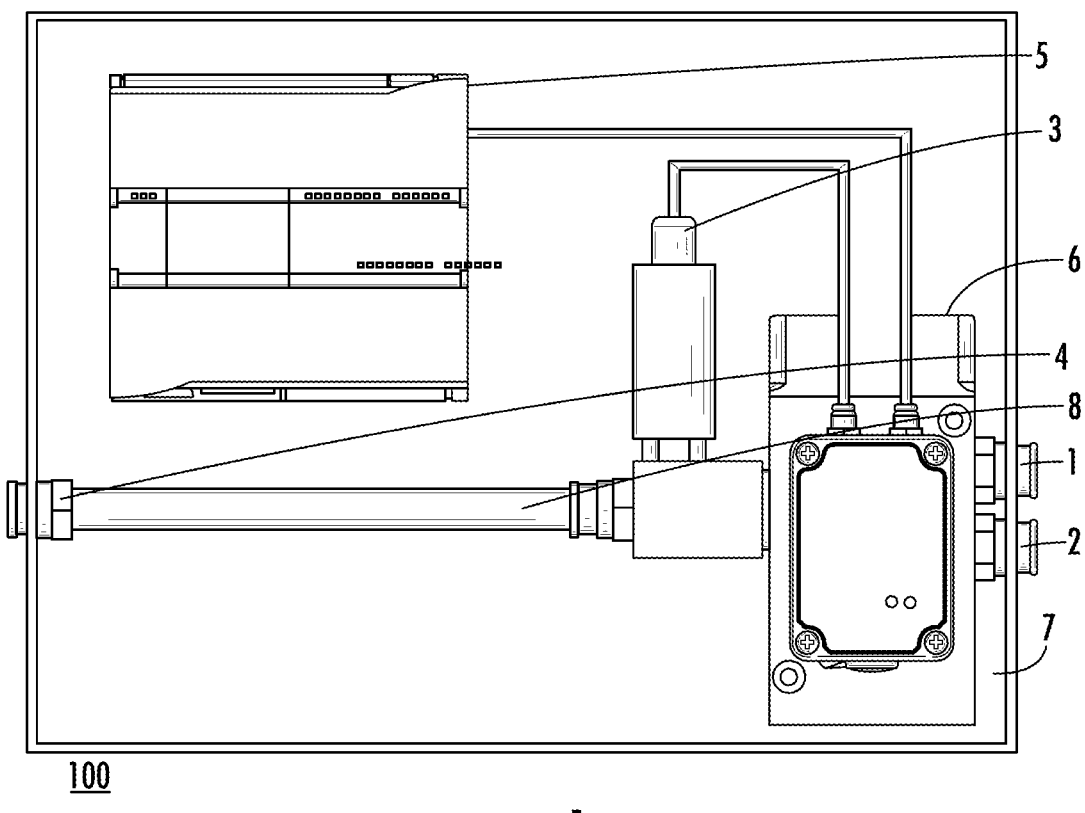
FIG. 1 depicts a control system according to an exemplary embodiment.

A preferred embodiment relates to a control unit, comprising a first connector configured to connect a proportional pressure regulator to a positive pressure supply; a second connector configured to connect the proportional pressure regulator to a negative pressure supply; at least one sensor configured to detect an amount of air flow (volume per unit of time), positive or negative, within an air flow line connected to an output of the proportional pressure regulator; a third connector configured to connect the air flow line to an air side of a diaphragm; and a controller programmed to control at least an opening and closing function of the proportional pressure regulator to attain a desired amount air flow (volume per unit of time), positive or negative, within the air flow line.

Another preferred embodiment relates to a method of actuating a diaphragm pump comprising selecting a volume or size of the pump; selecting a volume of fluid to be displaced by the diaphragm pump over a given period of time; selecting a duration of a pumping operation, which together with the desired volume of fluid to be displaced over said duration, generates a performance profile appropriate for a specific application; actuating the pumping operation by alternating a supply of positive and negative air flow in an air flow line connected at one end to an air side of the diaphragm pump and connected at an opposite end to an output of an air flow regulator; monitoring an amount of air flow within the air flow line to maintain or alter a volume of air flowing per unit of time within the air flow line; optionally, monitoring a position of the diaphragm at both ends of its displacement; and optionally, altering the volume of air flowing per unit of time within the air flow line to influence either the position of the diaphragm at one or both ends of its displacement or a duration of a partial or full cycle of displacement or both.

Yet another preferred embodiment relates to a method of controlling a diaphragm pump, comprising actuating a pumping operation of fluid from a first container by alternating a supply of positive and negative air flow to an air side of a diaphragm pump through an air flow line connected to an output of an air flow regulator; suctioning fluid from the first container by applying a supply of negative air flow to the air side of the diaphragm pump; regulating a duration of a partial or full cycle of displacement of the diaphragm pump; filtering the fluid suctioned from the first container; and extracting the filtered fluid so as to direct part of the fluid back to the first container and to direct part of the fluid to a second container.

A further preferred embodiment relates to a method of controlling a diaphragm pump with a controller, comprising alternating between applying positive and negative air flow to an air side of a diaphragm pump to actuate pumping of a fluid associated with a bioreactor; suctioning fluid from the bioreactor by applying negative air flow to the air side of the diaphragm pump; filtering the fluid suctioned from the bioreactor; extracting the filtered fluid to direct same to a container; and regulating a duration of partial or full cycle of displacement of the diaphragm pump, wherein the controller controls delivery of filtered fluid to the container in accordance with a process requirement.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

Filtration of biological fluids may be performed to separate blood into blood cells and plasma, among other implementations. For biomedical applications, it is important to be able to effectively clean the systems used for such filtration, so as to achieve sterile or substantially sterile conditions and protect against contamination, in accordance with Good Manufacturing Practice (GMP) guidelines. For example, alternating tangential flow systems include stainless steel components which are sterilized by steaming or by gamma irradiation. In particular, "single use" components of alternating tangential flow systems may be sterilized via gamma irradiation.

Alternating tangential flows of fluid may be used to perform filtering. More particularly, by alternating a tangential flow of fluid through a filter element, continuous filtration may be achieved. An alternating tangential flow system is described, for example, in U.S. Pat. No. 6,544,424 to Shevitz, the entire contents of which are incorporated herein for the background, apparatuses and technical content therein.

Filtration may be performed for purification, selective removal of unwanted constituents, and/or for maintaining a culture in perfusion at a high cell concentration. Various types of filters may be used, including hollow fiber filters containing a plurality of hollow fibers bundled together. Filtrating using the aforementioned alternating tangential flow may be carried out, for example, by a diaphragm pump flow in which positive and negative air flows are delivered in an alternating manner for activating liquid transfer. Current systems do not precisely modulate the duration of the transition between the positive and negative air flows or the amount of air flow. Moreover, current systems typically involve many components in complicated assemblies, which are difficult to maintain. The embodiments of the present disclosure, on the other hand, allow for precise control over the duration of the transition and amount, and allow for self-cleaning, among other benefits, as described in more detail below.

Figure 2:
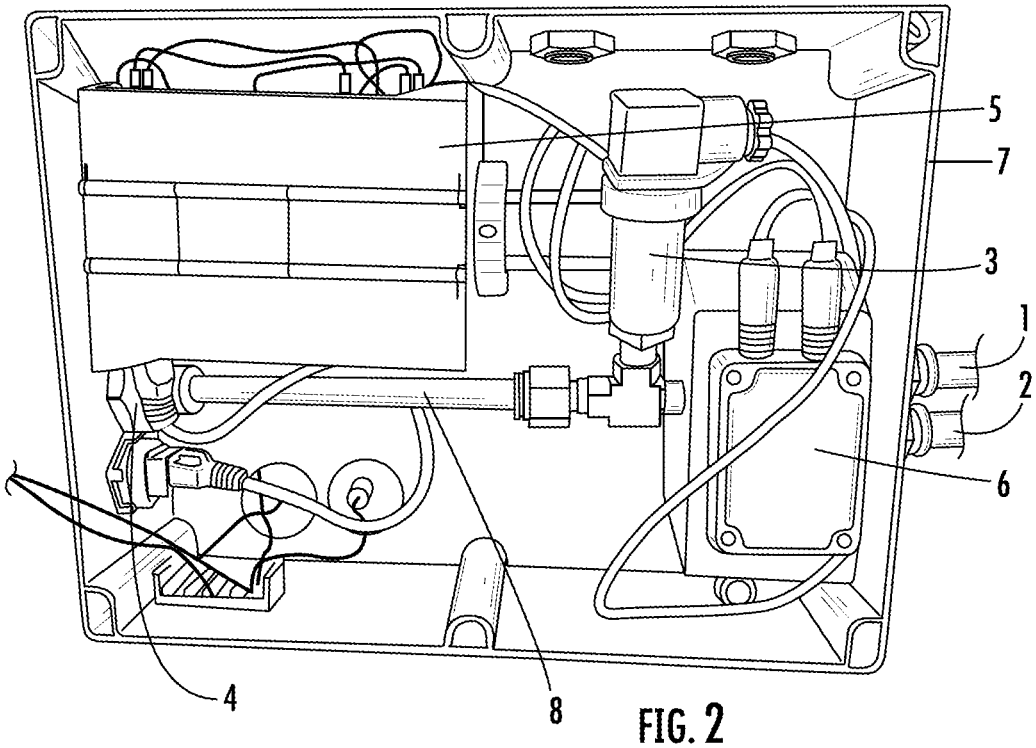
FIG. 2 depicts the control system shown in FIG. 1 in which a side panel of a housing is removed to reveal one configuration of elements within the housing.

FIG. 1 depicts a system 100 according to an exemplary embodiment. Certain components of system 100 shown in FIG. 1 may be provided within a housing 7. However, it should be appreciated that in certain embodiments, the system 100 may include components outside of the housing 7 which may be communicated, directly or indirectly, with components inside the housing 7. The system 100 includes a first connector configured to connect a proportional pressure regulator 6, which is contained within the housing 7, to a positive pressure supply 1. The proportional pressure regulator 6 may also be referred to as a proportional pressure valve. In at least one embodiment, the proportional pressure regulator 6 is a TR Pneumatic Pressure Control System, Model TR-010-g10-s, made by Enfield® Technologies of Shelton, Conn., USA. The system further includes a second connector configured to connect the proportional pressure regulator 6 to a negative pressure supply 2. The positive pressure supply 1 and negative pressure supply 2 are configured to provide, respectively, positive and negative air flow, as discussed in more detail below. The configuration of the positive and negative air pressure supplies 1, 2 is such that the air flow to the diaphragm is not restricted, thus allowing operation under lower incoming positive and negative pressures, thereby enhancing system safety. FIG. 2 depicts an exemplary representation of the system 100, in which a side panel of the housing is removed.

The system 100 includes at least one sensor 3 configured to detect an amount of air flow (volume per unit of time), positive or negative, within an air flow line 8 in the housing 7, and a third connector configured to connect the housing to an air side of a diaphragm pump. More specifically, the air flow line 8 is provided in the housing and is arranged between the proportional pressure regulator 6 and the third connector, such that the air flow line 8 is connected to an output of the proportional pressure regulator 6. The air flow line 8 imparts air flow that acts on the diaphragm pump. Further still, the system includes a controller (as may also be referred to as a control system, control module or control unit) 5 which is programmed to control at least an opening and closing function of the proportional pressure regulator 6 to attain a desired amount of air flow (volume per unit of time), positive or negative, within the air flow line 8.

Further, the controller 5 is programmed to regulate the flow of fluid of a diaphragm pump by controlling the positive and negative air flow applied via the third connector mentioned above. Accordingly, the controller 5 regulates operation of the diaphragm pump. Further, the controller 5 may adjust a flow of fluid from the diaphragm pump, in order to satisfy a process requirement. For example, in response to a setting inputted by a user, the controller 5 may cause the diaphragm pump to output a specified volume of fluid within a predetermined time period (e.g., 100 L in one day). An operator may provide an input to the controller 5 to specify a desired amount of outputted volume, and the controller 5 is programmed to control the diaphragm pump to achieve the desired amount. For example, the controller 5 is programmed to determine a number of pumping cycles (e.g., a number of cycles per minute) to achieve a specified output in accordance with the user input. Further, the controller 5 is configured to adjust operation of the pump and the supply of positive and negative air flow to account for variations. For example, over a time period such as one day, there may be changes in fluid viscosity over time, and the controller 5 is programmed to automatically control the fluid flow to account for such changes, in order to achieve the flow output specified by a user.

The controller may include a processor or microprocessor configured to run an operating system, an application-specific integrated circuit (ASIC), a field-programmable gate array (FPGA), etc., or combinations thereof. The controller may include memory which may include, but is not limited to, electronic, optical, magnetic, or any other storage or transmission device capable of providing a processor, ASIC, FPGA, etc. with program instructions. The memory may include a memory chip, Electrically Erasable Programmable Read-Only Memory (EEPROM), erasable programmable read only memory (EPROM), flash memory, or any other suitable memory from which the controller can read instructions. The instructions may include code from any suitable programming language.

Further, in certain embodiments, a user interface is provided where users of the control system 100 can input and/or monitor various facets of the control system 100 and operation of associated pumps. For example, the user interface may be programmed to display one or more graphical outputs of data received and analyzed by controller 5. The user interface may also display other data stored in the memory of controller 5, including data relating to the duration and amount of positive and negative air flow supplied by the positive pressure supply 1 and negative pressure supply 2, respectively, at each of a plurality of process steps. Other information that may be shown on the user interface includes data, showing minimum and maximum air flow amounts and volume, including tolerance ranges for air flow. Further still, additional parameters that may be displayed to the user at the user interface include a flow rate and a cycle time for one or more process steps.

Further still, the user interface of certain exemplary embodiments permits the user to control starting or stopping of a control process carried out by the controller 5. In some embodiments, starting and stopping functions may be controlled via buttons provided on a touch-screen display, for example. The user interface also allows for input (entry) of specified control parameters. For example, a desired amount of positive or negative pressure may be inputted by the user at the user interface of controller 5. The desired amount of positive or negative air flow is associated with a position of the diaphragm at both ends of its displacement when the diaphragm is connected to the housing 7.

In particular, at the user interface, the user can instruct the controller 5 to apply a constant positive air flow to the first connector in housing 7, and to apply a constant negative air flow to the second connector, for example. The user may initially set a size (e.g., in terms of volume) of the diaphragm pump to which the third connector is connected. The controller 5 automatically resets a displacement volume of the diaphragm based on the pump size. Next, the user may set a volume of a fluid to be displaced by the diaphragm pump over a given period of time, where the flow rate is the product of the number of full cycles per minute and the displacement volume per cycle. The controller is further programmed to adjust a duration of a full cycle of the diaphragm's displacement over a single pumping cycle or a plurality of pumping cycles, and to control displacement of a volume of fluid over a predetermined time period.

Additionally, either manually or in accordance with an algorithm or mathematical recipe, the user may further input the desired duration of a pumping operation, which, together with the desired volume of fluid to be displaced over said duration, generates a performance profile appropriate for a specific application, such as cell harvesting, may be generated. The performance profile may be based at least in part on the determined duration of a partial or full cycle of displacement of one pump or a plurality of pumps. The sensor 3 monitors air flow for each step and allows for comparison of the actual detected air flow to a predetermined threshold (e.g., an air flow corresponding to an allowed pressure). Further, in at least one embodiment, control system 100 allows for pumping fluid through the pump in a constant or variable flow in accordance with the performance profile. The performance profile is based on the determined duration and intensity for the plurality of process steps. For example, the performance profile may be generated based on selections of a duration of a pumping operation, including predetermined amounts of positive and negative air flow at a given process step. The controller 5 also allows for the user to adjust a degree of opening and/or closing of the regulator 6 in accordance with the duration of a partial or full cycle of displacement of the diaphragm pump, as may be carried out in accordance with the performance profile. Further still, the controller 5 allows for regulating a transition from opening to closing of the proportional pressure regulator 6 in accordance with the transition between the application of the supply of positive and negative air flow. Thus, the 'changeover' between positive and negative air flow may be precisely controlled. In particular, the controller 5 is configured to adjust a duration of a partial or full cycle of displacement of the diaphragm pump to satisfy a process requirement. Thus, the delivery of filtered fluid to a container may be controlled in accordance with the process requirement.

The control system 100 may also be configured to provide information to controller 5 from one or more sensors other than the sensor 3. For example, in at least one embodiment, the controller 5 is configured to receive an indication from at least one proximity sensor. The proximity sensor is disposed in a vicinity of the diaphragm and configured to detect a position of the diaphragm at one or both ends of its displacement (i.e., the displacement achieved at end positions of the diaphragm under positive and negative pressure). For example, the controller 5 is responsive to an output of a proximity sensor disposed in a vicinity of the diaphragm and configured to detect at least a position of the diaphragm at an end of its displacement (a "bottom" displacement) at a transition from a negative air flow to a positive air flow, and/or a position of the diaphragm at an end of its displacement (a "top" displacement) at a transition from a positive air flow to a negative air flow. Thus, the proximity sensor provides information to the controller 5 indicating a relative position of the diaphragm. The controller 5 adjusts a rate of fluid flow responsive to detection of the position by the proximity sensor. In particular, end positions of the diaphragm may be continuously monitored by the proximity sensor.

The diaphragm position must attain its maximal end positions so as to achieve a full displacement per cycle and to achieve full flow over a given time period. When the controller 5 determines, based on information from the proximity sensor, that one or more end positions is not met, the controller is configured to automatically adjust the opening of regulator 6 to increase the air flow, positive or negative. The controller 5 may cause the system 100 to emit an audible warning when a fault is detected by the controller, for example, when the diaphragm fails to attain the correct position for a given number of cycles. By way of further example, the controller 5 may receive information from a probe that is configured to detect a property of fluid flowing in the system 100, such as a glucose probe designed to indicate a glucose content of the fluid.

Furthermore, the control system 100 may also be configured to provide information to controller 5 from one or more sensors other than the pressure or proximity sensor. For example, in at least one embodiment, the controller 5 is configured to receive an indication from at least one liquid flow meter (a flow sensor) which is configured to detect an amount of fluid flow and/or diaphragm pump displacement. The flow is directly related to the diaphragm pump displacement controlled by positive and negative air flow. An additional flow meter (a flow sensor) on a filtrate side informs the user of the volume of the final product at any given time.

Moreover, at least one embodiment allows for a cleaning function to be carried out. In particular, the controller 5 controls the pressure supplies 1, 2 so as to deliver a burst of air pressure at a specified time so as to clean a filter of the pump. The controller 5 is programmed to cause the pump to perform a periodic filter cleaning cycle so as to remove unwanted particulates or debris from the filter. The cleaning cycle may be initiated manually, e.g., by selecting a 'clean cycle' option on the user interface, or automatically, e.g., when the controller determines based on data collection or a time interval since the last cleaning that the cleaning cycle should be performed. Further, the controller is programmed to cause the respective pressure supplies 1, 2 to supply at least one of positive or negative air flow at a first flow rate, and to clean the filter by delivering at least one burst of air flow at a second flow rate that is greater than the first flow rate. For example, the filter can be cleaned by applying a negative air flow and then delivering at least one burst of positive air flow at a second flow rate that is greater than the first flow rate. In at least one embodiment, a burst of air flow may be provided at a second rate that is at least twice as much as the first flow rate, for example. Additionally, cleaning can be performed using the pump. For example, the controller 5 may control the pump to have a short increase in pumping flow with a return to a lower constant flow rate, which may beneficially increase the filter life expectancy. In particular, the pump advances the flow of the filtrate to a second container, and the pump can stop or run in reverse to increase the back pressure, thereby creating a backflow, and generate a desired cleaning effect. Further, an efficient cleaning process may be carried out by utilizing both the air burst and pump flow control as described above in conjunction with each other. Further still, the controller 5 may control the timing of a burst of fluid flow, in addition to stopping or running the pump in reverse, as part of a cleaning process.

In addition, the controller 5 is programmed to controlling a timing of air pressure delivery to achieve a predetermined amount of air flow delivered to the air flow line in the housing 7. That is, in addition to a specified quantity and flow rate, the user may also input timing information (start, stop, duration) at the user interface. For example, the user may input a start and stop time to define a predetermined time period, and then the controller may effectuate control of the pressure supplies 1, 2 to output a continuous flow of air over a predetermined time period. In particular, the controller 5 regulates the air flow, positive or negative, so as to output an air flow at a first rate for a first period of time and output an air flow at a second rate for a second period of time, where the first period is shorter than the second period, and the first rate is higher than the second rate, or vice versa.

As mentioned above, in at least one embodiment, the controller is configured to perform a control for an alternating tangential flow pump. However, in at least one embodiment, the controller is configured to activate a tangential filtration flow in a continuous manner, rather than a reciprocating action. Further, in at least one embodiment, the controller is configured to cause an independent pump to operate according to an alternating tangential filtration flow function or a tangential filtration flow function by activating and controlling the independent pump. When the pump is operated according to the tangential filtration flow function, the controller performs an initiation process to cause the pump to begin the tangential filtration flow. Thereafter, the controller performs monitoring of the flow. In such embodiments, the proportional pressure regulator 6 is not actuated when the tangential filtration flow function is carried out.

Figure 3:
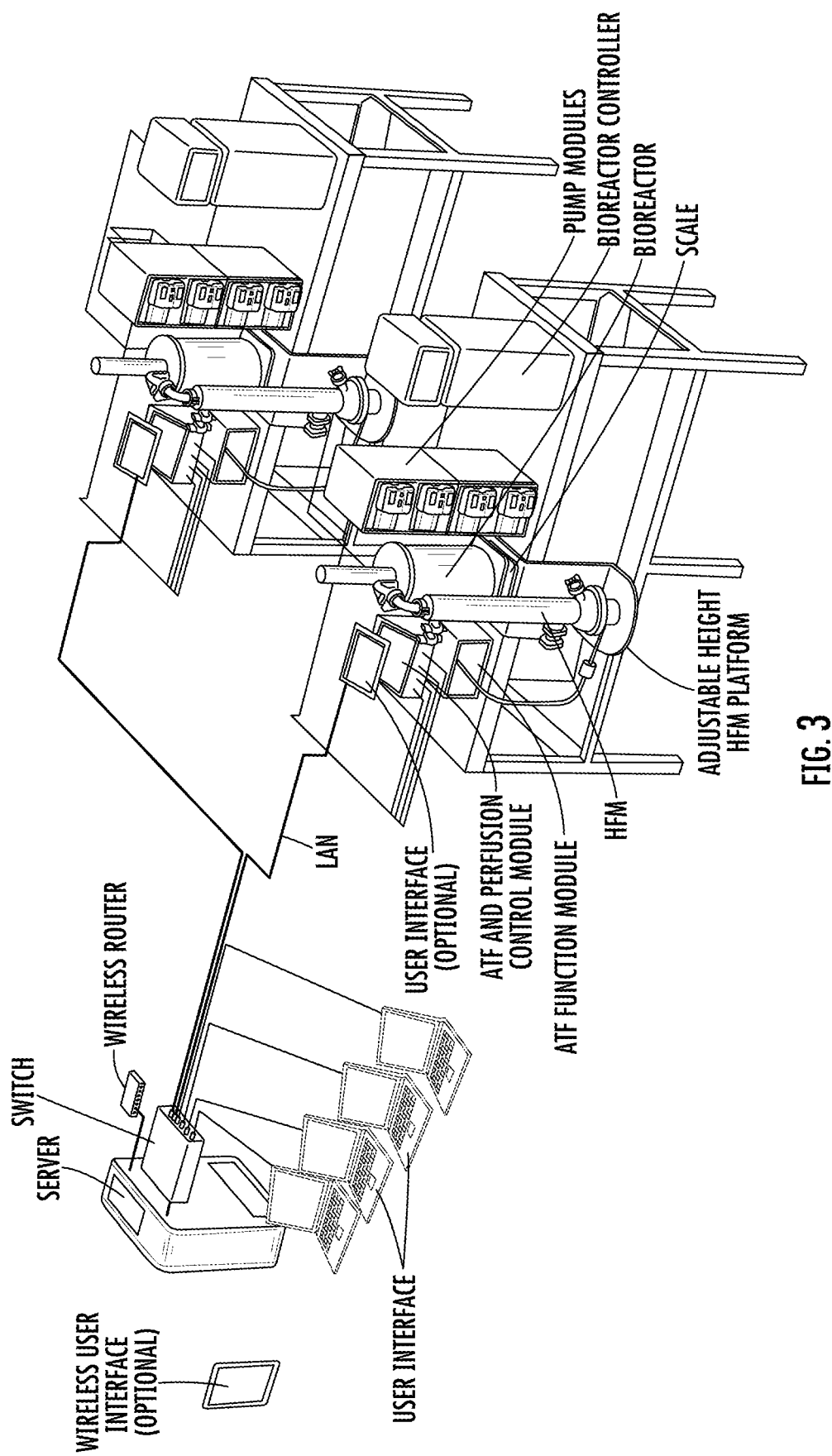
FIG. 3 depicts an alternating tangential flow control system according to an exemplary embodiment.

Turning now to FIG. 3, the system 100 shown in FIG. 1 may be provided in a bioreactor control system, according to an exemplary embodiment. The bioreactor control system of at least one embodiment is a multiplexed system, and may be included with a bioreactor having multiple pumping modules or one controller 5 services two or more bioreactors. In particular, in at least one embodiment, the housing 7 may house a plurality of pumping modules allowing for connection with multiple pumping modules. The controller 5 determines an operating speed of each pump. Other components of the bioreactor control system include a bioreactor, a scale, a hollow filter module and a platform for the same.

Further, the control system allows for a user to initiate a perfusion process. The perfusion process includes supplying media and supplying glucose when glucose is not present in the media, or not present in a desired quantity. The perfusion process further includes performing cell separation, permeation harvesting, and cell bleeding. To maintain a constant reactor volume, the aforementioned perfusion process steps must be coordinated. For example, media should be added at substantially the same rate at which permeate flows out of the system. In addition, the rate of media addition may be adjusted in accordance with the glucose content and the cell bleed rate, to ensure that the reactor has a constant volume. Cell bleeding and/or the addition of glucose are performed intermittently to maintain a desired cell density. In addition, cell separation itself is accomplished using an alternating tangential flow. The alternating tangential flow is established by the action of an oscillating diaphragm which passes the cell culture back and forth through hollow fiber membranes of a filter. The permeate pump flow rate may be synchronized with the diaphragm action to achieve a desired flow of permeate.

Figure 5:
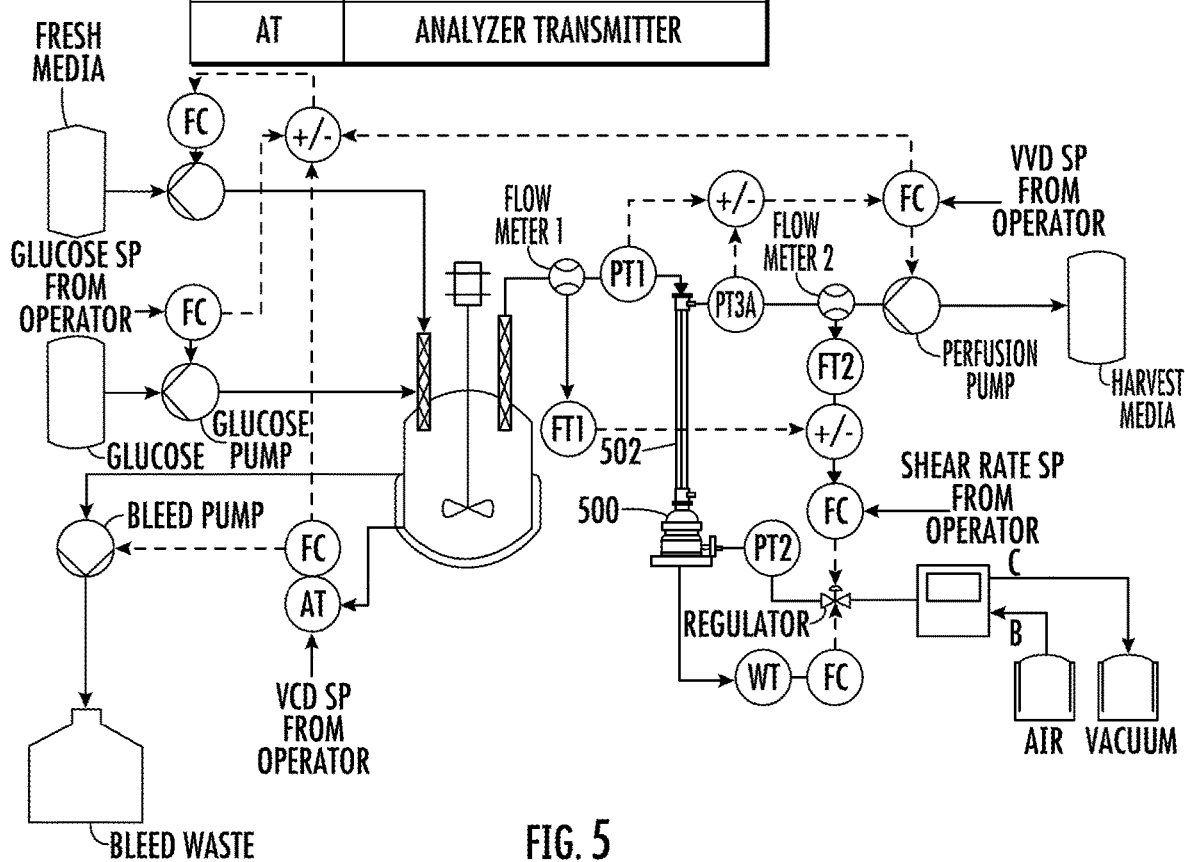
FIG. 5 depicts a schematic diagram according to an exemplary embodiment.

FIG. 5 depicts a schematic diagram of a bioreactor control system according to an exemplary embodiment. The bioreactor control system includes a plurality of pumps, including a media pump, a glucose pump, a bleed pump, and a perfusion pump. A plurality of flow meters may be used by one controller (e.g., controller 5).

As further shown in FIG. 5, a vessel containing fresh media is connected to a media pump and at least one flow controller FC. A vessel containing glucose is connected to a glucose pump and another flow controller FC. The speed and timing of the flow of glucose may be controlled by the operator. The fresh media vessel, the glucose vessel, and their respective pumps are fluidly connected to a bioreactor, shown in the form of a jacketed mixing vessel in FIG. 5. One or more regulators may be used to control the flow direction of material to and from the bioreactor. Material flowing to or from the bioreactor may be weighed on using a weight transducer or weight sensor WT, and the measured weight may be transmitted to the controller or displayed visually on a scale indicator separate from a controller. In addition, the bioreactor is communicated with an analyzer transmitter AT and a flow controller FC downstream of the bioreactor. The analyzer transmitter AT and the flow controller FC downstream of the bioreactor are configured to be connected to a bleed pump. The bleed pump is in turn configured to discharge waste to a bleed waste tank. A fluid passage connects the diaphragm regulator to the bioreactor, with a flow meter disposed in the fluid passage to measure fluid characteristics of fluid which flows out from the bioreactor.

The system further includes a positive air pressure supply (shown with supply line B) and a negative air pressure supply (shown with supply line C) that are connected to a regulator (corresponding to the proportional pressure regulator 6). For the sake of illustration, the regulator in FIG. 5 is shown outside of the enclosure. The regulator is connected to the perfusion pump and to at least one flow meter (flow transducer or flow sensor). For example, as shown in FIG. 5, a flow transducer FT1 is provided in the vicinity of the bioreactor, while a flow transducer FT2 is provided in the vicinity of the perfusion pump. The perfusion pump is fluidly connected to a vessel containing harvest media. At least one flow controller (e.g., a controller such as controller 5) is configured to receive volume and speed settings which may be inputted by an operator, e.g., at a user interface. Pressure transducers (pressure sensors) PT1, PT2, PT3A may be disposed to respectively measure the pressure between the bioreactor and the filter 502, between the filter 502 and the regulator, and between the filter 502 and the perfusion pump, for example. Further, at least one flow controller is configured to receive, as an input, a desired shear rate for fluid flow within the system, which may be inputted at the user interface. Further still, the flow controller is configured to receive, as an input, a vessel value per day. The vessel value per day is a filtered volume amount which generally corresponds to the volume of the vessel. The controller 5 is also configured to receive parameters such as a valuable cell density as an input.

Such embodiments may be practiced in a networked environment using logical connections to one or more remote computers having processors. Persons skilled in the art will appreciate that such network computing environments may encompass many types of computers, including personal computers, hand-held devices, multi-processor systems, microprocessor-based or programmable consumer electronics, network PCs, minicomputers, mainframe computers, and so on. Implementations may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

The bioreactor control system also includes at least one communications unit that may be coupled to a switch and a router for providing a communication link between the system and a network. As such, the communications unit enables the processor to communicate, wired or wirelessly, with other electronic systems coupled to the network. For instance, the communications unit may be coupled to an Ethernet line that connects the system to the Internet or another network. In other implementations, the communications unit may be coupled to an antenna (not shown) and provides functionality to transmit and receive information over a wireless communication interface with the network.

In various implementations, the communications unit may include one or more transceivers configured to perform data communications in accordance with one or more communications protocols including but not limited to WLAN protocols (e.g., IEEE 802.11 a/b/g/n/ac/ad, IEEE 802.16, IEEE 802.20, etc.). Accordingly, the bioreactor control system allows for monitoring and control of pumping operations throughout the networked environment. Data collection and analysis for multiple pumping modules may also be carried out. Further, information such as a sensed pressure level from a diaphragm pressure sensor which is built in or attached to a diaphragm housing may be transmitted to controller 5. Sensed data indicative of an amount of fluid flow at a housing holding the diaphragm pump may also be obtained and provided to the controller.

By way of further example, the controller 5 may be connected, via the network, to another controller, such as an independent controller of a bioreactor vessel. Furthermore, in at least one embodiment, the controller 5 may be in communication with a suite of sensors which monitor operating temperature, fluid level, and rheological properties of the fluid. For example, an optical turbidity monitor can be provided which sends turbidity data to the controller 5, for example. In addition, information about the composition of the biological fluid may also be relayed to the controller 5 and conveyed to the user via the user interface. For example, the density of cells in the biological fluid may be determined and displayed to the user. Additionally, data analysis may be performed so as to determine a performance profile based on data from a plurality of pumps of the pumping system of the bioreactor control system. Further, statistical distributions of interest may be generated based on data from a plurality of pumps, and may be used to assess pump system performance.

Further still, the bioreactor control system includes a plurality of containers (vessels). For example, in at least one embodiment, the control system contains a first vessel in which unfiltered material is stored, and a second vessel in which filtered material is stored. The material may be a biological fluid, such as a fluid containing animal, human or microbial cells. The pump 500 is activated so as to pump 500 part of the fluid from the first vessel through a filter 502, and to deliver the filtered fluid to the second vessel. More specifically, by applying negative air flow to the air flow line 8 in the housing 7, fluid may be suctioned from the first vessel. The delivery of fluid from the first vessel to the diaphragm pump 500 or another vessel may be controlled in accordance with alternating the supply of positive and negative air flow amounts. Expulsion of fluid from the pump 500 or vessel can be controlled in the same manner as delivery of the fluid. Accordingly, in at least one embodiment, biological fluid is suctioned from a bioreactor to a vessel, and a portion of the fluid may be returned to the bioreactor, while another portion may be directed to a vessel (e.g., a second container). In some embodiments, the second container may be refrigerated. For example, the filter 502 (e.g., a hollow fiber filter) may be used to separate biological fluid and direct part of the filtrates to the second vessel. The alternating tangential flow may be used to continuously filter the fluid until it reaches the second vessel.

Additionally, the pump can be operated to pump part of the fluid from the first vessel back to the first vessel (a return flow). Further, the controller 5 is operable to permit or restrict the flow of fluid from the second container, to permit or restrict the backflow (return flow) of fluid from the second container to the first container. The controller 5 may restrict a backflow when a backflow function not used to clean the filter (i.e., when the control system does not employ the backflow function temporarily, in a cleaning state).

Figure 4:
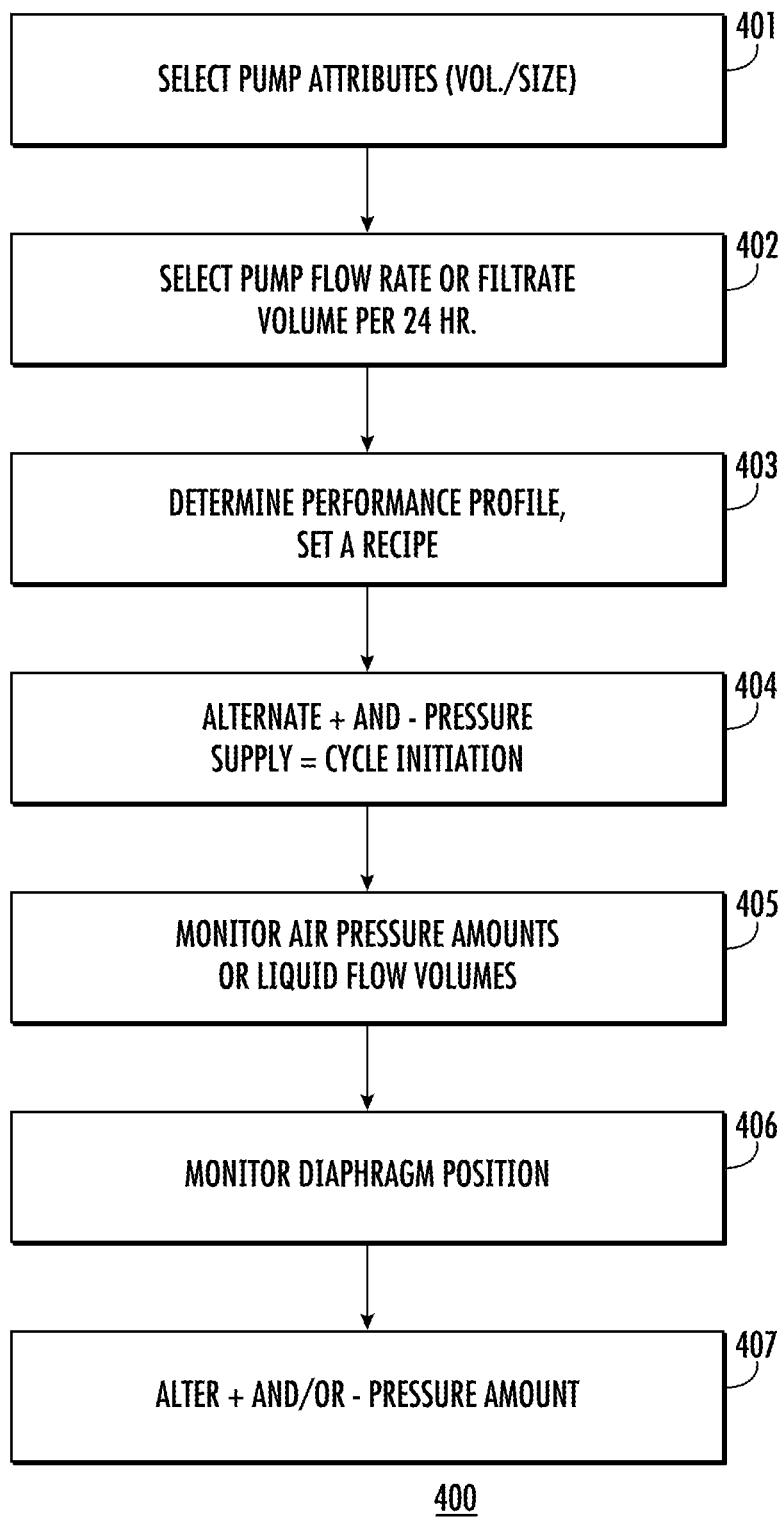
FIG. 4 depicts a control method according to an exemplary embodiment.

FIG. 4 depicts a control process 400 according to an embodiment. The process 400 relates to an actuation operation of a pump which is equipped with a diaphragm. The process includes selecting a volume or size of the pump (step 401) and selecting a flow rate (volume per minute) (step 402). The process further includes selecting a duration of a pumping operation, including predetermined amounts of positive and negative air flow at a given process step, to generate a performance profile appropriate for a specific application (step 403). Additionally, the process includes actuating the pumping operation by alternating a supply of positive and negative air flow through a regulator housed within a housing (step 404). Further, the process includes monitoring an amount of positive or negative air flow within the air flow line in the housing to maintain or alter a volume of air flowing per unit of time within the air flow line (step 405). Optionally, additional process step(s) may be carried out. For example, the control process 400 further includes optionally monitoring a position of the diaphragm at one or both ends of its displacement (step 406) and optionally altering the volume of air flowing per unit of time within the air flow line to influence either the position of the diaphragm at one or both ends of its displacement or a duration of a partial or full cycle of displacement or both (step 407).

While this specification contains specific implementation details, these should not be construed as limitations on the scope of what may be claimed, but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, the separation of various system components in the implementations described above should not be understood as requiring such separation in all implementations, and it should be understood that the described components and systems can generally be integrated in a single product or packaged into multiple products.

As utilized herein, the terms "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The terms "coupled," "connected," and the like as used herein mean the joining of two components directly or indirectly to one another. Such joining may be stationary (e.g., permanent) or moveable (e.g., removable or releasable). Such joining may be achieved with the two components or the two components and any additional intermediate components being integrally formed as a single unitary body with one another or with the two components or the two components and any additional intermediate components being attached to one another.

The terms "fluidly coupled," "in fluid communication," and the like as used herein mean the two components or objects have a pathway formed between the two components or objects in which a fluid, such as water, air, biological fluid, etc., may flow, either with or without intervening components or objects. Examples of fluid couplings or configurations for enabling fluid communication may include piping, channels, or any other suitable components for enabling the flow of a fluid from one component or object to another.

It is important to note that the construction and arrangement of the system shown in the various exemplary implementations is illustrative only and not restrictive in character. All changes and modifications that come within the spirit and/or scope of the described implementations are desired to be protected. It should be understood that some features may not be necessary and implementations lacking the various features may be contemplated as within the scope of the application, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A filtration system, comprising:
a filter assembly;
a vessel coupled to the filter assembly;
a pump coupled to the filter assembly for moving a flow of material between the filter assembly and the vessel;
an air flow line coupled to a diaphragm portion of the pump having a diaphragm;
a regulator coupled to the air flow line for controlling air flow through the air flow line, the regulator further coupled to a positive pressure supply for supplying a positive air flow to the diaphragm portion of the pump via the air flow line, the regulator also coupled to a negative pressure supply for providing a negative air flow from the diaphragm portion of the pump through the air flow line;
a sensor coupled to the air flow line for sensing the air flow through the air flow line; and
a controller coupled to the sensor and the regulator, the controller including a processor arranged and configured to execute instructions to control the regulator to control the air flow through the air flow line, wherein controlling the air flow through the air flow line controls the pump to thereby control the flow of material between the filter assembly and the vessel, and wherein controlling the air flow through the air flow line includes altering a volume of air flow per unit of time within the air flow line to influence either a position of the diaphragm portion of the pump at one or both ends of its displacement or a duration of a partial or full cycle of displacement of the diaphragm, or both.

2. The system of claim 1, wherein the processor is programmed to execute instructions for receiving sensed air flow information from the sensor, comparing the sensed air flow information to a predetermined threshold, and to adjust the air flow through the air flow line to thereby control the flow of the material between the filter assembly and the vessel.

3. The system of claim 1, wherein the processor is programmed to execute instructions for automatically controlling the flow of material between the vessel and the filter assembly to account for variations in material viscosity over time to achieve a flow output specified by a user.

4. The system of claim 1, wherein the processor is programmed to execute instructions to control the regulator to adjust the air flow through the air flow line to control operation of the pump to account for variations in material viscosity over time.

5. The system of claim 1, wherein the regulator comprises a proportional pressure regulator.

6. The system of claim 1, wherein the filter assembly includes a hollow fiber filter, the vessel is a bioreactor, and the pump is controlled to induce alternating tangential flow within the filter assembly.

7. A filtration system, comprising:
a filter assembly;
a diaphragm pump coupled to the filter assembly for moving a flow of material through the filter assembly;
an air flow line coupled to a diaphragm portion of the diaphragm pump having a diaphragm;
a regulator coupled to the air flow line for controlling air flow through the air flow line, the regulator coupled to positive and negative pressure supplies for supplying positive and negative air flow, respectively, to the diaphragm portion of the diaphragm pump via the air flow line;
a sensor coupled to the air flow line for sensing the air flow through the air flow line; and
a controller coupled to the sensor and the regulator, the controller including a processor arranged and configured to execute instructions to control the regulator to control the air flow through the air flow line, wherein controlling the air flow through the air flow line controls the pump to thereby control the flow of material through the filter assembly, and wherein controlling the air flow through the air flow line includes altering a volume of air flow per unit of time within the air flow line to influence either a position of the diaphragm of the pump at one or both ends of its displacement or a duration of a partial or full cycle of displacement of the diaphragm, or both.

8. The system of claim 7, wherein the processor is programmed to execute instructions for receiving sensed air flow information from the sensor, comparing the sensed air flow information to a predetermined threshold, and to adjust the air flow through the air flow line to thereby control the flow of the material through the filter assembly.

9. The system of claim 7, wherein the processor is programmed to execute instructions for automatically controlling the flow of material through the filter assembly to account for variations in material viscosity over time to achieve a flow output specified by a user.

10. The system of claim 7, wherein the processor is programmed to execute instructions to control the regulator to adjust the air flow through the air flow line to control operation of the pump to account for variations in material viscosity over time.

11. The system of claim 7, wherein the processor is programmed to execute instructions for controlling the regulator to thereby regulate a duration of a partial or a full cycle of the pump.

12. The system of claim 7, wherein the regulator comprises a proportional pressure regulator.

13. The system of claim 7, wherein the filter assembly includes a hollow fiber filter, and the pump is controlled to induce alternating tangential flow within the filter assembly.

14. A method for controlling a filter system, comprising:
flowing a material between a vessel and a filter assembly using a pump;
sensing air flow through an air flow line coupled to a diaphragm portion of the pump having a diaphragm; and
based on said sensed air flow, adjusting the air flow through the air flow line to alter a volume of air flow per unit of time within the air flow line to influence either a position of the diaphragm of the pump at one or both ends of its displacement or a duration of a partial or full cycle of displacement of the diaphragm, or both, to control operation of the pump to control the flow of the material between the filter assembly and the vessel.

15. The method of claim 14, wherein adjusting the air flow through the air flow line comprises controlling a positive air flow pressure or a negative air flow pressure through the air flow line via a regulator coupled to the air flow line.

16. The method of claim 14, further comprising comparing the sensed air flow to a predetermined threshold and adjusting the air flow through the air flow line to thereby control the flow of the material between the filter assembly and the vessel.

17. The method of claim 14, further comprising automatically controlling the flow of material between the vessel and the filter assembly to account for variations in material viscosity over time to achieve a flow output specified by a user.

18. The method of claim 14, further comprising controlling the diaphragm pump to induce alternating tangential flow within the filter assembly. The following is an examiner's statement of reasons for allowance: Each of independent claims 1, 8 and 15, and thus claims dependent therefrom, remain distinguished over all of the prior art of record for reasons persuasively argued in Applicant's Remarks of May 25, 2023 concerning, a controller operable for controlling, or a method of adjusting, the air flow line of the diaphragm pump to alter a volume of air flow per unit of time within the air flow line to influence either a position of the diaphragm portion of the pump at one or both ends of its displacement or a duration of a partial or full cycle of displacement of the diaphragm, or both.

* * * * *